US012616647B2

(12) United States Patent
Roudot et al.

(10) Patent No.: US 12,616,647 B2
(45) **Date of Patent: *May 5, 2026**

(54) NON-PULVERULENT ANTISUN COMPOSITION COMPRISING A POLAR OIL PHASE AND HYDROPHOBIC SILICA AEROGEL PARTICLES

(71) Applicant: L'OREAL, Paris (FR)

(72) Inventors: Angelina Roudot, Le Kremlin Bicetre (FR); Anne Falip, Alfortville (FR); Florence L'Alloret, Paris (FR)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 18/430,571

(22) Filed: Feb. 1, 2024

(65) Prior Publication Data

US 2024/0197607 A1 Jun. 20, 2024

Related U.S. Application Data

(63) Continuation of application No. 14/376,687, filed as application No. PCT/EP2013/051556 on Jan. 28, 2013, now abandoned.

(60) Provisional application No. 61/599,774, filed on Feb. 16, 2012.

(30) Foreign Application Priority Data

Feb. 6, 2012 (FR) ....................................... 1251073

(51) Int. Cl.

| | |
|---|---|
| ***A61K 8/25*** | (2006.01) |
| ***A61K 8/02*** | (2006.01) |
| ***A61K 8/34*** | (2006.01) |
| ***A61K 8/35*** | (2006.01) |
| ***A61K 8/37*** | (2006.01) |
| ***A61K 8/49*** | (2006.01) |
| ***A61K 8/58*** | (2006.01) |
| ***A61Q 17/04*** | (2006.01) |

(52) U.S. Cl.

CPC ............ *A61K 8/585* (2013.01); *A61K 8/0279* (2013.01); *A61K 8/25* (2013.01); *A61K 8/342* (2013.01); *A61K 8/35* (2013.01); *A61K 8/37* (2013.01); *A61K 8/375* (2013.01); *A61K 8/4966* (2013.01); *A61Q 17/04* (2013.01); *A61K 2800/412* (2013.01)

(58) Field of Classification Search

CPC .... A61K 8/25; A61K 8/585; A61K 2800/412; A61K 8/0279; A61K 8/0283; A61Q 17/04

See application file for complete search history.

(56) References Cited

U.S. PATENT DOCUMENTS

| | | | | |
|---|---|---|---|---|
| 10,105,292 B2* | 10/2018 | Fageon | .................... | A61Q 5/00 |
| 11,318,072 B2* | 5/2022 | Pierre | .................. | A61K 8/0241 |
| 11,497,705 B2* | 11/2022 | Clavel | ...................... | A61Q 1/06 |
| 12,121,602 B2* | 10/2024 | Salomao | .................. | A61K 8/33 |
| 2009/0196894 A1 | 8/2009 | Ehlis et al. | | |

FOREIGN PATENT DOCUMENTS

| | | |
|---|---|---|
| WO | 0103663 A1 | 1/2001 |
| WO | 2009120602 A1 | 10/2009 |
| WO | 2013068237 A1 | 5/2013 |

OTHER PUBLICATIONS

Lucidity Anhydrous Sunscreen, Cosmetics & Toiletries Science Applied, posted Sep. 3, 2009 http://dir.cosmeticsandtoiletries.com/detal/formula.hrml?id-350.

Dow Corning: "Dow Corning VM-2270 Aerogel Fine Particles", Internet Citation, Apr. 2009, pp. 1-5.

* cited by examiner

*Primary Examiner* — Bethany P Barham
*Assistant Examiner* — Danielle Johnson
(74) *Attorney, Agent, or Firm* — POLSINELLI PC

(57) ABSTRACT

The present invention relates to a non-pulverulent composition comprising, in a cosmetically acceptable medium:

at least one oil phase containing:
at least one polar oil
at least one lipophilic organic UV-screening agent
at least hydrophobic silica aerogel particles
the said composition comprising less than 5% by weight of non-volatile non-cyclic silicone oil relative to the total weight of the composition.

The invention also relates to a cosmetic process for caring for and/or making up human keratin materials, in particular the skin of the body or of the face or the hair, comprising at least the application, to the surface of the keratin material, of at least one composition as defined above.

24 Claims, No Drawings

NON-PULVERULENT ANTISUN COMPOSITION COMPRISING A POLAR OIL PHASE AND HYDROPHOBIC SILICA AEROGEL PARTICLES

CROSS-REFERENCE TO RELATED APPLICATIONS

This application claims priority to and is a continuation of U.S. patent application Ser. No. 14/376,687, filed on Aug. 5, 2014, which is a National Stage Entry of PCT/EP2013/051556, filed Jan. 28, 2013, which claims the benefit under 35 U.S.C. § 119(e) of the filing date of U.S. Provisional Patent Application No. 61/599,774, filed on Feb. 16, 2012, and priority to French Application No. 1251073, filed on Feb. 6, 2012, the entirety contents of each are herein incorporated by reference.

The present invention relates to a non-pulverulent composition comprising, in a cosmetically acceptable medium:

a) at least one oil phase containing
  (i) at least one polar oil,
  (ii) at least one lipophilic organic UV-screening agent,
b) at least hydrophobic silica aerogel particles, the said composition comprising less than 5% by weight of non-volatile non-cyclic silicone oil relative to the total weight of the composition.

The invention also relates to a cosmetic process for caring for and/or making up human keratin materials, in particular the skin of the body or of the face or the hair, comprising at least the application, to the surface of the keratin material, of at least one composition as defined above.

It is known that radiation with wavelengths of between 280 nm and 400 nm permits tanning of the human epidermis and that radiation with wavelengths of between 280 and 320 nm, known as UV-B rays, harms the development of a natural tan. Exposure is also liable to bring about a detrimental change in the biomechanical properties of the epidermis, which is reflected by the appearance of wrinkles, leading to premature ageing of the skin.

It is also known that UV-A rays with wavelengths of between 320 and 400 nm penetrate more deeply into the skin than UV-B rays. UV-A rays cause immediate and persistent browning of the skin. Daily exposure to UV-A rays, even of short duration, under normal conditions can result in damage to elastin and collagen fibres, which is reflected by a modification of the microrelief of the skin, the appearance of wrinkles and uneven pigmentation (liver spots, heterogeneity of the complexion).

Many photoprotective compositions have been proposed to date for overcoming the effects induced by UVA and/or UVB radiation. They generally contain organic or inorganic UV-screening agents that operate, according to their intrinsic chemical nature and their intrinsic properties, by absorption, reflection or scattering of the UV radiation. They generally contain mixtures of liposoluble organic screening agents and/or water-soluble UV-screening agents combined with metal oxide pigments such as titanium dioxide or zinc oxide.

Many cosmetic compositions intended for the photoprotection (UV-A and/or UV-B) of the skin have been provided to date. Formulations that afford users easy application to the skin are most particularly desired. These screening cosmetic compositions must moreover satisfy the regulations as regards the protection factor and especially the European regulations on antisun products, in particular on the protection ratio between UV-B and UV-A radiation and more particularly the SPF/PPD ratio, which must be less than 3.

The efficacy of antisun compositions for UV-B protection is generally expressed by the sun protection factor (SPF), which is expressed mathematically by the ratio of the dose of UV radiation necessary to reach the erythemal threshold with the UV-screening agent to the dose of UV radiation necessary to reach the erythemal threshold without UV-screening agent. This factor thus concerns the efficacy of the protection having a spectrum of biological action centred in the UV-B range and consequently gives an account of the protection with regard to this UV-B radiation.

To characterize the protection with regard to UV-A radiation, the PPD (persistent pigment darkening) method, which measures the colour of the skin observed 2 to 4 hours after exposure of the skin to UV-A radiation, is particularly recommended and used. This method has been adopted since 1996 by the Japanese Cosmetic Industry Association (JCIA) as the official test procedure for the UV-A labelling of products and is frequently used by test laboratories in Europe and the United States (Japan Cosmetic Industry Association Technical Bulletin. Measurement Standards for UVA protection efficacy. Issued Nov. 21, 1995 and effective as of Jan. 1, 1996).

The UV-APPD sun protection factor (UV-Appd PF) is expressed mathematically by the ratio of the dose of UV-A radiation necessary to reach the pigmentation threshold with the UV-screening agent (MPPDp) to the dose of UV-A radiation necessary to reach the pigmentation threshold without UV-screening agent (MPPDnp).

$$\text{UV-A}_{PPD}PF = \frac{MPPD_p}{MPPD_{np}}$$

It is known that a relatively large amount of UV-screening agents has to be used to achieve a significant level of screening efficacy against UV-A and UV-B radiation. However, these UV-screening agents have the following drawbacks when they are formulated at a high content: instability of the formulations and sensory defects such as a greasy and/or tacky feel.

It is known practice to use in antisun formulations hydrophobic modified silicas of the type such as silica dimethyl silylate and silica silylate, especially in patent application WO 01/03663, for affording water remanence to the formulation, or alternatively in patent application WO 2007/148292, as oil thickeners. These are not hydrophobic silica aerogel particles.

There is still a need for photoprotective cosmetic compositions with a good level of screening efficacy which is obtained using limited contents of UV-screening agents and that have good cosmetic properties on application.

The Applicant has discovered, surprisingly, that this object can be achieved by using hydrophobic silica aerogel particles in a non-pulverulent composition comprising, in a cosmetically acceptable medium:

a) at least one oil phase containing
  (i) at least one polar oil,
  (ii) at least one lipophilic organic UV-screening agent and
b) at least hydrophobic silica aerogel particles, the said composition comprising less than 5% by weight of non-volatile non-cyclic silicone oil relative to the total weight of the composition.

This discovery forms the basis of the present invention.

The present invention thus relates to a non-pulverulent composition comprising, in a cosmetically acceptable medium:

a) at least one oil phase containing
 (i) at least one polar oil,
 (iii) at least one lipophilic organic UV-screening agent
b) at least hydrophobic silica aerogel particles, the said composition comprising less than 5% by weight of non-volatile non-cyclic silicone oil relative to the total weight of the composition.

It also relates to a cosmetic method for caring for and/or making up human keratin materials, in particular the skin of the body or of the face or the hair, comprising at least the application, to the surface of the keratin material, of at least one composition as defined above.

The term "human keratin materials" means the skin (of the body, face and around the eyes), hair, eyelashes, eyebrows, bodily hair, nails, lips or mucous membranes.

The term "cosmetically acceptable medium" means any medium that is compatible with the skin and/or its integuments, which has a pleasant colour, odour and feel and which does not cause any unacceptable discomfort (smarting, tautness or redness) liable to dissuade the consumer from using this composition.

The term "lipophilic organic UV-screening agent" means an organic molecule that is capable of screening out UV radiation between 290 and 400 nm and which can be dissolved in the molecular or dispersed state in an oil phase in order to obtain a macroscopically homogeneous phase.

The term "organic molecule" is understood to mean any molecule comprising, in its structure, one or more carbon atoms.

For the purposes of the present invention, the term "non-pulverulent composition" means any composition that is not in the form of a loose or compact powder.

The term "compact powder" means a mass of product whose cohesion is at least partly provided by compacting during the manufacture. In particular, by carrying out a measurement using a TA.XT.plus Texture Analyser sold by Stable Micro Systems, the compact powder according to the invention can advantageously exhibit a resistance to pressure of between 0.1 and 1 kg and in particular between 0.2 and 0.8 kg, with respect to the surface area of the spindle used (in the case in point, 7.07 $mm^2$). This resistance is measured by causing an SMS P/3 flat-ended cylindrical spindle in contact with the powder to move over a distance of 2 mm at a speed of 0.5 mm/second; more generally, this powder is obtained by compacting. The term "compact powder" should be understood more specifically to mean that these powders have a Shore A hardness, measured using a Zwick hardness tester, which varies, according to the intensity of the shades under consideration, from 12 to 30° Shore A.

The term "loose powder" means a mass of product that is capable of collapsing under its own weight; such a mass being formed by particles that are predominantly isolated and mobile relative to each other.

Aerogel Particles of Hydrophobic Silica

Aerogels are ultralight porous materials which were first produced by Kristler in 1932.

They are generally synthesized by a sol-gel process in a liquid medium and then dried by extraction with a supercritical fluid. The supercritical fluid most commonly used is supercritical $CO_2$. This type of drying makes it possible to avoid shrinkage of the pores and of the material.

Other types of drying also make it possible to obtain porous materials starting from gel, namely (i) drying by freeze drying, which consists in solidifying the gel at low temperature and in then subliming the solvent, and (ii) drying by evaporation. The materials thus obtained are referred to respectively as cryogels and xerogels. The sol-gel process and the various drying operations are described in detail in Brinker C. J. and Scherer G. W., Sol-Gel Science, New York, Academic Press, 1990.

The term "hydrophobic silica" means any silica whose surface is treated with silylating agents, for example halogenated silanes such as alkylchlorosilanes, siloxanes, in particular dimethylsiloxanes such as hexamethyldisiloxane, or silazanes, so as to functionalize the OH groups with silyl groups Si—Rn, for example trimethylsilyl groups.

Preferably, the hydrophobic aerogel particles that may be used in the present invention advantageously have a specific surface area per unit of mass (SM) ranging from 200 to 1500 $m^2/g$, preferably from 600 to 1200 $m^2/g$ and better still from 600 to 800 $m^2/g$ and/or have an oil-absorbing capacity, measured at the wet point, ranging from 5 to 18 ml/g of particles, preferably from 6 to 15 ml/g and better still from 8 to 12 ml/g.

The absorption capacity measured at the wet point, denoted Wp, corresponds to the amount of water that needs to be added to 100 g of particles in order to obtain a homogeneous paste.

It is measured according to the "wet point" method or method of determination of oil uptake of a powder described in standard NF T 30-022. It corresponds to the amount of oil adsorbed onto the available surface of the powder and/or absorbed by the powder by measurement of the wet point, described below:

An amount m=2 g of powder is placed on a glass plate and the oil (isononyl isononanoate) is then added dropwise. After addition of 4 to 5 drops of oil to the powder, mixing is carried out using a spatula, and addition of oil is continued until conglomerates of oil and powder have formed. From this point, the oil is added at the rate of one drop at a time and the mixture is subsequently triturated with the spatula. The addition of oil is stopped when a firm, smooth paste is obtained. This paste must be able to be spread over the glass plate without cracks or the formation of lumps. The volume Vs (expressed in ml) of oil used is then noted.

The oil uptake corresponds to the ratio Vs/m.

The aerogel particles of hydrophobic silica used according to the present invention are preferably aerogel particles of silylated silica (INCI name: silica silylate).

The preparation of aerogel particles of hydrophobic silica modified at the surface by silylation is further described in the document U.S. Pat. No. 7,470,725.

Use will be made in particular of hydrophobic silica aerogel particles surface-modified with trimethylsilyl groups.

The hydrophobic aerogel particles that may be used in the present invention advantageously have a size, expressed as the mean diameter (D[0.5]), of less than 1500 μm, preferably ranging from 1 to 30 μm, preferably from 5 to 25 μm, better still from 5 to 20 μm and even better still from 5 to 15 μm.

The specific surface area per unit of weight can be determined by the nitrogen absorption method, known as the BET (Brunauer-Emmett-Teller) method, described in The Journal of the American Chemical Society, Vol. 60, page 309, February 1938, which corresponds to international standard ISO 5794/1 (appendix D). The BET specific surface area corresponds to the total specific surface area of the particles under consideration.

The sizes of the aerogel particles according to the invention can be measured by static light scattering using a commercial particle size analyser such as the MasterSizer 2000 machine from Malvern. The data are processed on the basis of the Mie scattering theory. This theory, which is exact for isotropic particles, makes it possible to determine, in the case of non-spherical particles, an "effective" particle diameter. This theory is described in particular in the publication by Van de Hulst, H. C., "Light Scattering by Small Particles", Chapters 9 and 10, Wiley, New York, 1957.

According to one advantageous embodiment, the hydrophobic aerogel particles used in the present invention have a specific surface area per unit of mass (SM) ranging from 600 to 800 $m^2/g$ and a size, expressed as the volume mean diameter (D[0.5]), ranging from 5 to 20 μm and better still from 5 to 15 μm.

The hydrophobic aerogel particles used in the present invention may advantageously have a tamped density p ranging from 0.04 $g/cm^3$ to 0.10 $g/cm^3$ and preferably from 0.05 $g/cm^3$ to 0.08 $g/cm^3$.

In the context of the present invention, this density can be assessed according to the following protocol, known as packed density protocol:

40 g of powder are poured into a graduated measuring cylinder and then the measuring cylinder is placed on a Stav 2003 device from Stampf Volumeter. The measuring cylinder is subsequently subjected to a series of 2500 packing actions (this operation is repeated until the difference in volume between two consecutive tests is less than 2%) and then the final volume Vf of packed powder is measured directly on the measuring cylinder.

The tamped density is determined by the ratio: mass m/Vf, in this instance 40/Vf (Vf being expressed in $cm^3$ and m in g).

According to one embodiment, the hydrophobic aerogel particles used in the present invention have a specific surface area per unit of volume SV ranging from 5 to 60 $m^2/cm^3$, preferably from 10 to 50 $m^2/cm^3$ and better still from 15 to 40 $m^2/cm^3$.

The specific surface area per unit of volume is given by the relationship: SV=SM*p, where p is the tamped density, expressed in $g/cm^3$, and $S_M$ is the specific surface per unit of mass, expressed in $m^2/g$, as defined above.

As hydrophobic silica aerogels that may be used in the invention, an example that may be mentioned is the aerogel sold under the name VM-2260 (INCI name: Silica silylate) by the company Dow Corning, the particles of which have a mean size of about 1000 microns and a specific surface area per unit of mass ranging from 600 to 800 $m^2/g$.

Mention may also be made of the aerogels sold by Cabot under the references Aerogel TLD 201, Aerogel OGD 201 and Aerogel TLD 203, Enova Aerogel MT 1100 and Enova Aerogel MT 1200.

Use will more particularly be made of the aerogel sold under the name VM-2270 (INCI name: Silica silylate) by the company Dow Corning, the particles of which have a mean size ranging from 5 to 15 microns and a specific surface area per unit of mass ranging from 600 to 800 $m^2/g$.

The silica aerogel particles in accordance with the invention are preferably present in the cosmetic composition in an amount of active material ranging from 0.1% to 15% by weight and more preferentially from 0.5% to 10% by weight relative to the total weight of the composition.

Oil Phase

The compositions in accordance with the invention comprise at least one oil phase comprising at least one polar oil.

The term "oil phase" means a fatty phase that is in liquid form.

The term "liquid" refers to a composition that is liquid at room temperature (25° C.) and atmospheric pressure (760 mmHg).

The term "polar oil" means any lipophilic compound having, at 25° C., a solubility parameter $\delta_d$ characteristic of dispersive interactions of greater than 16 and a solubility parameter $\delta_p$ characteristic of polar interactions strictly greater than 0. The solubility parameters $\delta_d$ and $\delta_p$ are defined according to the Hansen classification. For example, these polar oils may be chosen from esters, triglycerides and ethers.

The definition and calculation of the solubility parameters in the Hansen three-dimensional solubility space are described in the paper by C. M. Hansen: "The three dimensional solubility parameters", J. Paint Technol. 39, 105 (1967).

According to this Hansen space:

$\delta_D$ characterizes the London dispersion forces derived from the formation of dipoles induced during molecular impacts;

$\delta_p$ characterizes the Debye interaction forces between permanent dipoles and also the Keesom interaction forces between induced dipoles and permanent dipoles;

$\delta_h$ characterizes the specific interaction forces (such as hydrogen bonding, acid/base, donor/acceptor, etc.); and $\delta_a$ is determined by the equation: $\delta_a=(\delta_p{}^2+\delta_n{}^2)^{1/2}$.

The parameters $\delta_p$, $\delta_n$, $\delta_D$ and $\delta_a$ are expressed in $(J/cm^3)^{1/2}$.

These polar oils may be of plant, mineral or synthetic origin.

The polar oils will preferably be chosen from non-volatile polar hydrocarbon-based oils.

The term "polar hydrocarbon-based oil" means a polar oil formed essentially from, or even constituted by, carbon and hydrogen atoms, and optionally oxygen and nitrogen atoms, and not containing any silicon or fluorine atoms. It may contain alcohol, ester, ether, carboxylic acid, amine and/or amide groups.

The term "non-volatile oil" means an oil that remains on the skin or the keratin fibre at room temperature and atmospheric pressure for at least several hours, and that especially has a vapour pressure of less than $10^{-3}$ mmHg (0.13 Pa).

The non-volatile polar hydrocarbon-based oil may be chosen especially from the following oils:

hydrocarbon-based polar oils such as phytostearyl esters, such as phytostearyl oleate, phytostearyl isostearate and lauroyl/octyldodecyl/phytostearyl glutamate (Ajinomoto, Eldew PS203), triglycerides consisting of fatty acid esters of glycerol, in particular the fatty acids of which may have chain lengths ranging from $C_4$ to $C_{36}$, and especially from $C_{18}$ to $C_{36}$, these oils possibly being linear or branched, and saturated or unsaturated; these oils may especially be heptanoic or octanoic triglycerides, wheatgerm oil, sunflower oil, grapeseed oil, sesame seed oil (820.6 g/mol), corn oil, apricot oil, castor oil, shea oil, avocado oil, olive oil, soybean oil, sweet almond oil, palm oil, rapeseed oil, cottonseed oil, hazelnut oil, macadamia oil, jojoba oil, alfalfa oil, poppy oil, pumpkin oil, marrow oil, blackcurrant oil, evening primrose oil, millet oil, barley oil, *quinoa* oil, rye oil, safflower oil, candlenut oil, passionflower oil or musk rose oil; shea butter; or alternatively caprylic/capric acid triglycerides, for instance those sold by the company Stearineries Dubois or those sold under the names Miglyol 810®, 812® and 818® by the company Dynamit Nobel;

synthetic ethers containing from 10 to 40 carbon atoms, such as dicaprylyl ether;

hydrocarbon-based esters of formula RCOOR' in which RCOO represents a carboxylic acid residue comprising from 2 to 40 carbon atoms, and R' represents a hydrocarbon-based chain containing from 1 to 40 carbon atoms, such as cetostearyl octanoate, isopropyl alcohol esters, such as isopropyl myristate or isopropyl palmitate, ethyl palmitate, 2-ethylhexyl palmitate, isopropyl stearate or isostearate, isostearyl isostearate, octyl stearate, diisopropyl adipate, heptanoates, and especially isostearyl heptanoate, alcohol or polyalcohol octanoates, decanoates or ricinoleates, for instance propylene glycol dioctanoate, cetyl octanoate, tridecyl octanoate, 2-ethylhexyl 4-diheptanoate and palmitate, alkyl benzoate, polyethylene glycol diheptanoate, propylene glycol 2-diethyl hexanoate, and mixtures thereof, $C_{12}$ to $C_{15}$ alcohol benzoates, hexyl laurate, neopentanoic acid esters, for instance isodecyl neopentanoate, isotridecyl neopentanoate, isostearyl neopentanoate and 2-octyldodecyl neopentanoate, isononanoic acid esters, for instance isononyl isononanoate, isotridecyl isononanoate and octyl isononanoate, oleyl erucate, isopropyl lauroyl sarcosinate, diisopropyl sebacate, isocetyl stearate, isodecyl neopentanoate, isostearyl behenate, and myristyl myristate;

polyesters obtained by condensation of an unsaturated fatty acid dimer and/or trimer and of diol, such as those described in patent application FR 0 853 634, in particular such as dilinoleic acid and 1,4-butanediol. Mention may especially be made in this respect of the polymer sold by Biosynthis under the name Viscoplast 14436H (INCI name: dilinoleic acid/butanediol copolymer), or else copolymers of polyols and of dimer diacids, and esters thereof, such as Hailuscent ISDA;

polyol esters and pentaerythritol esters, for instance dipentaerythrityl tetrahydroxystearate/tetraisostearate;

fatty alcohols containing from 12 to 26 carbon atoms, for instance octyldodecanol, 2-butyloctanol, 2-hexyldecanol, 2-undecylpentadecanol and oleyl alcohol;

higher $C_{12}$-$C_{22}$ fatty acids, such as oleic acid, linoleic acid and linolenic acid, and mixtures thereof;

fatty acids containing from 12 to 26 carbon atoms, for instance oleic acid;

dialkyl carbonates, the two alkyl chains possibly being identical or different, such as dicaprylyl carbonate sold under the name Cetiol CC® by Cognis; and non-volatile oils of high molecular mass, for example between 400 and 10 000 g/mol, in particular between 650 and 10 000 g/mol, for instance:

i) vinylpyrrolidone copolymers such as the vinylpyrrolidone/1-hexadecene copolymer, Antaron V-216 sold or manufactured by the company ISP (MW=7300 g/mol), ii) esters such as:

a) linear fatty acid esters with a total carbon number ranging from 35 to 70, for instance pentaerythrityl tetrapelargonate (MW=697.05 g/mol), b) hydroxylated esters such as polyglycerol-2 triisostearate (MW=965.58 g/mol), c) aromatic esters such as tridecyl trimellitate (MW=757.19 g/mol), $C_{12}$-$C_{15}$ alcohol benzoate, the 2-phenylethyl ester of benzoic acid, and butyloctyl salicylate, d) esters of $C_{24}$-$C_{28}$ branched fatty acids or fatty alcohols such as those described in patent application EP-A-0 955 039, and especially triisoarachidyl citrate (MW=1033.76 g/mol), pentaerythrityl tetraisononanoate (MW=697.05 g/mol), glyceryl triisostearate (MW=891.51 g/mol), glyceryl tris(2-decyl) tetradecanoate (MW=1143.98 g/mol), pentaerythrityl tetraisostearate (MW=1202.02 g/mol), polyglyceryl-2 tetraisostearate (MW=1232.04 g/mol) or else pentaerythrityl tetrakis(2-decyl)tetradecanoate (MW=1538.66 g/mol), e) esters and polyesters of dimer diol and of monocarboxylic or dicarboxylic acid, such as esters of dimer diol and of fatty acid and esters of dimer diol and of dimer dicarboxylic acid, such as Lusplan DD-DA5® and Lusplan DD-DA7® sold by the company Nippon Fine Chemical and described in patent application US 2004-175 338, the content of which is incorporated into the present application by reference, and mixtures thereof.

Preferably the non-volatile hydrocarbon-based polar oil is chosen from capric/caprylic acid triglycerides, $C_{12}$-$C_{15}$ alcohol benzoates, diisopropyl sebacate, isopropyl lauroyl sarcosinate, dicaprylyl carbonate, the 2-phenylethyl ester of benzoic acid, butyloctyl salicylate, 2-octyldodecyl neopentanoate, dicaprylyl ether, isocetyl stearate, isodecyl neopentanoate, isononyl isononate, isopropyl myristate, isopropyl palmitate, isostearyl behenate, myristyl myristate, octyl palmitate and tridecyl trimellitate, and mixtures thereof.

Even more preferentially, the non-volatile hydrocarbon-based polar oil is chosen from capric/caprylic acid triglycerides, $C_{12}$-$C_{15}$ alcohol benzoates, diisopropyl sebacate and octyldodecanol, and mixtures thereof.

According to one particular mode, the non-volatile hydrocarbon-based oil may be chosen from liquid lipophilic organic UV-screening agents.

The term "liquid" refers to a composition that is liquid at room temperature (25° C.) and atmospheric pressure (760 mmHg).

Preferably, the polar oil(s) and in particular the non-volatile hydrocarbon-based oil(s) in accordance with the invention are present in a content ranging from 5% to 95% by weight and even more particularly from 10% to 90% by weight relative to the total weight of the composition.

The fatty phase may also contain at least one volatile or non-volatile silicone oil and/or fluoro oil.

The term "silicone oil" means an oil containing at least one silicon atom, and especially containing Si—O groups.

The term "fluoro oil" means an oil containing at least one fluorine atom.

For the purposes of the invention, the term "volatile oil" means an oil that is capable of evaporating on contact with the skin or the keratin fibre in less than one hour, at room temperature and atmospheric pressure. The volatile oil(s) of the invention are volatile cosmetic oils, which are liquid at room temperature, having a non-zero vapour pressure at room temperature and atmospheric pressure, ranging in particular from 0.13 Pa to 40 000 Pa ($10^{-3}$ to 300 mmHg), in particular ranging from 1.3 Pa to 13 000 Pa (0.01 to 100 mmHg) and more particularly ranging from 1.3 Pa to 1300 Pa (0.01 to 10 mmHg).

The compositions of the invention comprise less than 5% by weight of non-volatile non-cyclic silicone oil.

Preferably, the molecular weight of the non-cyclic silicone oil is between 500 and 100 000 g/mol.

The non-cyclic silicone oils preferably have a viscosity advantageously chosen in the range from 4 to 10 000 $mm^2/s$ at 25° C., preferably from 4 to 5000 $mm^2/s$, better still from 4 to 1000 $mm^2/s$ and even better still from 4 to 200 $mm^2/s$.

The method for measuring the viscosity used in the invention for characterizing the silicone oils according to the invention may be the "kinematic viscosity at 25° C. raw product CID-012-01" or the "Viscosity Ubbelohde DIN 51562-1 PV04001 25° C.".

The non-cyclic silicone oil may have a refractive index of greater than 1.3 and especially less than 1.6.

The non-cyclic silicone oils that may be used in the makeup compositions according to the present invention are represented by the general formula (I) below:

(I)

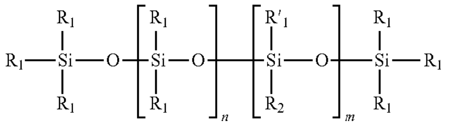

with:

$R_1$, which may be identical or different, representing:

i) a linear or branched ($C_1$-$C_{20}$)alkyl and particularly linear or branched $C_1$-$C_6$ group, such as methyl, ethyl, propyl or butyl; or ii) a hydroxyl group;

$R_2$ representing:

i) a linear or branched ($C_1$-$C_{20}$)alkyl group optionally interrupted and/or terminated with a heteroatom such as O, S or N; in particular, i) is a linear or branched $C_1$-$C_6$ alkyl group, such as methyl, ethyl, propyl or butyl;

ii) a ($C_1$-$C_9$)(poly)haloalkyl group, especially perfluoroalkyl, comprising from 1 to 9 halogen atoms, particularly fluorine, such as trifluoromethyl; and iii) the polysiloxane group $—O—[Si(R_1)_2—O]n'—Si(R_1)_3$ with $R_1$ as defined previously; $R'_1$ representing a radical $R_1$ or $R_2$ as defined previously;

m being an integer inclusively between 0 and 150 and preferably between 20 and 100;

n and n', which may be identical or different, being an integer inclusively between 1 and 300 and preferably between 1 and 100.

According to one preferred embodiment, R'1 represents the radical $R_1$, and more particularly a ($C_1$-$C_6$)alkyl group such as methyl.

According to one particular embodiment, m is 0.

According to another particular embodiment of the invention, $R_1$ is a methyl, and more particularly m is 0 and $R_1$ is a methyl.

According to one particular example of the invention, the non-cyclic silicone oils may be chosen from a fluorosilicone compound.

Fluorosilicone compounds that may especially be mentioned include those sold by the company Shin-Etsu under the names X22-819, X22-820, X22-821 and X22-822 or FL-100.

According to one preferred embodiment, the said non-cyclic silicone oil is a dimethicone corresponding to formula (II) below:

(II)

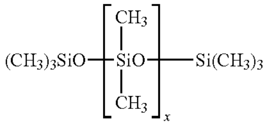

in this formula (II), x being an integer ranging from 1 to 50, better still from 1 to 20 and more specifically from 1 to 10. The molecular mass of such a compound may be, for example, approximately 770 g/mol. Preferably, x is equal to 8.

According to one particular embodiment, the non-cyclic silicone oil of general formula (I) or (II) is advantageously chosen from the oils sold by the company Dow Corning under the reference 200R Fluid 5 cSt® and under the references 200R Fluid 100 cSt®, Dow Corning 200 Fluid 350 cSt and Dow Corning 200 Fluid 200-350 cSt®.

The fatty phase of the compositions according to the invention may also comprise one or more volatile silicone oils.

Volatile silicone oils that may be mentioned, for example, include volatile linear or cyclic silicone oils, especially those with a viscosity≤ 8 centistokes (8×10-6 $m^2/s$) and especially containing from 2 to 7 silicon atoms, these silicones optionally comprising alkyl or alkoxy groups containing from 1 to 10 carbon atoms. As volatile silicone oils that may be used in the invention, mention may be made especially of octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane, and mixtures thereof.

The fatty phase of the compositions according to the invention may comprise one or more volatile hydrocarbon-based oils.

As volatile hydrocarbon-based oils that may be used according to the invention, mention may be made especially of hydrocarbon-based oils containing from 8 to 16 carbon atoms, and especially branched $C_8$-$C_{16}$ alkanes such as $C_8$-$C_{16}$ isoalkanes of petroleum origin (also known as isoparaffins), for instance isododecane (also known as 2,2,4,4,6-pentamethylheptane), isodecane, isohexadecane, and the alkanes described in the patent applications from the company Cognis WO 2007/068 371 or WO 2008/155 059 (mixtures of different alkanes differing by at least one carbon). These alkanes are obtained from fatty alcohols, which are themselves obtained from coconut oil or palm oil, the oils sold under the trade name Isopar or Permethyl, branched $C_8$-$C_{16}$ esters, isohexyl neopentanoate, and mixtures thereof.

The fatty phase of the compositions according to the invention may comprise one or more natural or synthetic waxes.

The term "wax" is understood to mean a compound which is solid or substantially solid at room temperature and which has a melting point generally of greater than 35° C.

Waxes that may be mentioned include carnauba wax, beeswax, hydrogenated castor oil, polyethylene waxes and polymethylene waxes, for instance the product sold under the name Cirebelle 303 by the company Sasol.

In the context of the anhydrous compositions, the oil phase may be present in the composition according to the invention in an amount ranging from 50% to 100% and better still from 60% to 100% by weight relative to the total weight of the composition.

In the case of oil-in-water or water-in-oil emulsions, the oil phase may be present in the composition according to the invention in an amount ranging from 10% to 90% and better still from 15% to 90% by weight relative to the total weight of the composition.

Lipophilic Organic Screening Agents

The lipophilic organic UV-screening agents are chosen especially from cinnamic derivatives; anthranilates; salicylic derivatives; dibenzoylmethane derivatives, camphor derivatives; benzophenone derivatives; β, β-diphenylacrylate derivatives; triazine derivatives; benzotriazole derivatives; benzalmalonate derivatives, especially those mentioned in patent U.S. Pat. No. 5,624,663; imidazolines; p-aminobenzoic acid (PABA) derivatives; benzoxazole derivatives as described in patent applications EP 0 832 642, EP 1 027 883, EP 1 300 137 and DE 101 62 844; screening polymers and screening silicones such as those described especially in patent application WO 93/04665; α-alkylstyrene-based dimers such as those described in patent application DE 198 55 649; 4,4-diarylbutadienes such as those described in patent applications EP 0 967 200, DE 197 46 654, DE 197 55 649, EP-A-1 008 586, EP 1 133 980 and EP 1 133 981; merocyanin derivatives such as those described in patent applications WO 04/006 878, WO 05/058 269, WO 06/032 741, FR 2 957 249 and FR 2 957 250; and mixtures thereof.

As examples of additional organic photoprotective agents, mention may be made of those denoted hereinbelow under their INCI name:

As examples of lipophilic organic UV-screening agents, mention may be made of those denoted hereinbelow under their INCI name:

Dibenzoylmethane Derivatives:

Butyl Methoxy Dibenzoylmethane or avobenzone, provided for sale under the trade name Parsol 1789 by DSM Nutritional Products, Para-Aminobenzoic Acid Derivatives:

- PABA,
- Ethyl PABA,
- Ethyl Dihydroxypropyl PABA,
- Ethylhexyl Dimethyl PABA sold in particular under the name Escalol 507 by ISP, Salicylic Derivatives:

- Homosalate sold under the name Eusolex HMS by Rona/EM Industries,
- Ethylhexyl salicylate sold under the name Neo Heliopan OS by Symrise, Cinnamic Derivatives:

- Ethylhexyl methoxycinnamate sold especially under the trade name Parsol MCX by DSM Nutritional Products,
- Isopropyl methoxycinnamate,
- Isoamyl p-methoxycinnamate sold under the trade name Neo Heliopan E 1000 by Symrise,
- Cinoxate,
- Diisopropyl Methylcinnamate, β,β-Diphenylacrylate Derivatives:

- Octocrylene sold especially under the trade name Uvinul N539 by BASF,
- Etocrylene sold in particular under the trade name Uvinul N35 by BASF.

Benzophenone Derivatives:

- Benzophenone-1 sold under the trade name Uvinul 400 by BASF,
- Benzophenone-2 sold under the trade name Uvinul D50 by BASF,
- Benzophenone-3 or oxybenzone sold under the trade name Uvinul M40 by BASF,
- Benzophenone-6 sold under the trade name Helisorb 11 by Norquay,
- Benzophenone-8 sold under the trade name Spectra-Sorb UV-24 by American Cyanamid,
- Benzophenone-12,
- n-hexyl 2-(4-diethylamino-2-hydroxybenzoyl)benzoate sold under the trade name
- Uvinul A+ or in the form of a mixture with octyl methoxycinnamate under the trade name Uvinul A+B by BASF,
- 1,1'-(1,4-piperazinediyl)bis[1-[2-[4-(diethylamino)-2-hydroxybenzoyl]phenyl]methanone (CAS 919803-06-8) in micronized or non-micronized form, Benzylidenecamphor Derivatives:

- 3-Benzylidene Camphor manufactured under the name Mexoryl SD by Chimex,
- 4-Methylbenzylidene Camphor sold under the name Eusolex 6300 by Merck,
- Polyacrylamidomethylbenzylidenecamphor manufactured under the name Mexoryl SW by Chimex.

Phenylbenzotriazole Derivatives:

- Drometrizole trisiloxane sold under the name Silatrizole by Rhodia Chimie,

Triazine Derivatives:

- bis-Ethylhexyloxyphenol methoxyphenyl triazine sold under the trade name Tinosorb S by BASF,
- Ethylhexyl triazone sold in particular under the trade name Uvinul T150 by BASF,
- Diethylhexyl Butamido Triazone sold under the trade name Uvasorb HEB by Sigma 3V,
- 2,4,6-Tris(dineopentyl 4'-aminobenzalmalonate)-s-triazine,
- 2,4,6-Tris(diisobutyl 4'-aminobenzalmalonate)-s-triazine,
- 2,4-Bis(dineopentyl 4'-aminobenzalmalonate)-6-(n-butyl 4'-aminobenzoate)-s-triazine, Anthranilic Derivatives:

- Menthyl anthranilate sold under the trade name Neo Heliopan MA by Symrise.

Imidazoline Derivatives:

- Ethylhexyl Dimethoxybenzylidene Dioxoimidazoline Propionate,

Benzalmalonate Derivatives:

- Dineopentyl 4'-methoxybenzalmalonate,
- Polyorganosiloxane containing benzalmalonate functions, for instance
- Polysilicone-15, sold under the trade name Parsol SLX by DSM, 4,4-Diarylbutadiene Derivatives:

- 1,1-Dicarboxy(2,2'-dimethylpropyl)-4,4-diphenylbutadiene,

Benzoxazole Derivatives:

- 2,4-Bis[4-[5-(1,1-dimethylpropyl)benzoxazol-2-yl]phenylimino]-6-[(2-ethylhexyl)imino]-1,3,5-triazine, sold under the name of Uvasorb K2A by Sigma 3V, and mixtures thereof.

Lipophilic Merocyanin Derivatives:

- Octyl 5-N,N-diethylamino-2-phenylsulfonyl-2,4-pentadienoate and mixtures thereof.

The Preferred Lipophilic Organic Screening Agents are Chosen from:

- Butyl Methoxy Dibenzoylmethane,
- Ethylhexyl Methoxycinnamate,
- Ethylhexyl salicylate,
- Homosalate,
- Butylmethoxydibenzoylmethane,
- Octocrylene,
- Benzophenone-3,
- n-Hexyl 2-(4-diethylamino-2-hydroxybenzoyl)benzoate,
- 4-Methylbenzylidene Camphor,
- Bis-Ethylhexyloxyphenol Methoxyphenyl Triazine,
- Ethylhexyl Triazone,
- Diethylhexyl Butamido Triazone,
- 2,4,6-Tris(dineopentyl 4'-aminobenzalmalonate)-s-triazine,
- 2,4,6-Tris(diisobutyl 4'-aminobenzalmalonate)-s-triazine,
- 2,4-Bis(di-neopentyl 4'-aminobenzalmalonate)-6-(n-butyl 4'-aminobenzoate)-s-triazine, Drometrizole Trisiloxane,
Polysilicone-15,
1,1-Dicarboxy(2,2'-dimethylpropyl)-4,4-diphenylbutadiene,
2,4-Bis[4-[5-(1,1-dimethylpropyl)benzoxazol-2-yl]phenylimino]-6-[(2-ethylhexyl)imino]-1,3,5-triazine,
and mixtures thereof.

The Preferred Lipophilic Organic Screening Agents are More Particularly Chosen from:

Butyl Methoxy Dibenzoylmethane,
Octocrylene,
Ethylhexyl Salicylate,
n-Hexyl 2-(4-diethylamino-2-hydroxybenzoyl)benzoate,
Bis-Ethylhexyloxyphenol Methoxyphenyl Triazine,
Ethylhexyl Triazone,
Diethylhexyl Butamido Triazone,
Drometrizole Trisiloxane, and mixtures thereof.

The lipophilic organic UV-screening agent(s) are preferably present in the compositions according to the invention at a content ranging from 0.1% to 40% by weight and in particular from 5% to 25% by weight relative to the total weight of the composition.

Galenical Forms

The compositions may be in the form of an anhydrous composition, especially the form of an oil, an anhydrous cream or an oily gel.

For the purposes of the invention, the term "anhydrous" means a composition whose content of free or added water is less than 3% and preferably whose content of added water is less than 1% by weight relative to the total weight of the composition, or even is free of water.

According to one particular form of the invention, the compositions may also comprise at least one aqueous phase and may in particular be in the form of a simple emulsion, especially an oil-in-water emulsion, a water-in-oil emulsion or a multiple emulsion (O/W/O or W/O/W emulsions).

More particularly, the aqueous compositions will be oil-in-water emulsions.

The aqueous phase may be a demineralized water or alternatively a floral water such as cornflower water and/or a mineral water such as Vittel water, Lucas water or La Roche Posay water and/or a spring water.

The emulsification processes that may be used are of the paddle or propeller, rotor-stator and HPH type.

To obtain stable emulsions with a low content of polymer (oil/polymer ratio >25), it is possible to do the dispersion in concentrated phase and then to dilute the dispersion with the rest of the aqueous phase.

It is also possible, via HHP (between 50 and 800 bar), to obtain stable dispersions with droplet sizes that may be as low as 100 nm.

The emulsions generally comprise at least one emulsifier chosen from amphoteric, anionic, cationic or nonionic emulsifiers, used alone or as a mixture. The emulsifiers are appropriately chosen according to the emulsion to be obtained (W/O or O/W).

When it is an emulsion, the aqueous phase of this emulsion may comprise a nonionic vesicular dispersion prepared according to known processes (Bangham, Standish and Watkins, J. Mol. Biol. 13, 238 (1965), FR 2 315 991 and FR 2 416 008).

The compositions according to the invention find their application in a large number of treatments, especially cosmetic treatments, of the skin, the lips and the hair, including the scalp, especially for protecting and/or caring for the skin, the lips and/or the hair, and/or for making up the skin and/or the lips.

The cosmetic compositions according to the invention may be used, for example, as makeup products.

The cosmetic compositions according to the invention may be used, for example, as care products and/or antisun protection products for the face and/or the body, of liquid to semi-liquid consistency, such as milks, more or less rich creams, cream-gels and pastes. They may optionally be packaged in aerosol form and may be in the form of a mousse or a spray.

The compositions according to the invention in the form of vaporizable fluid lotions in accordance with the invention are applied to the skin or the hair in the form of fine particles by means of pressurization devices. The devices in accordance with the invention are well known to those skilled in the art and comprise non-aerosol pump-dispensers or "atomizers", aerosol containers comprising a propellant and also aerosol pump-dispensers using compressed air as propellant. These devices are described in patents U.S. Pat. Nos. 4,077,441 and 4,850,517.

The compositions packaged in aerosol form in accordance with the invention generally contain conventional propellants, for instance hydrofluoro compounds, dichlorodifluoromethane, difluoroethane, dimethyl ether, isobutane, n-butane, propane or trichlorofluoromethane. They are preferably present in amounts ranging from 15% to 50% by weight relative to the total weight of the composition.

Another subject of the present invention consists of the use of the compositions according to the invention as defined above for the manufacture of products for the cosmetic treatment of the skin, the lips, the nails, the hair, the eyelashes, the eyebrows and/or the scalp, especially care products, antisun products and make-up products.

The cosmetic compositions according to the invention can be used, for example, as make-up products.

Adjuvants

The compositions in accordance with the present invention may also comprise one or more standard cosmetic adjuvants chosen from organic solvents, thickeners, softeners, humectants, opacifiers, stabilizers, emollients, fragrances, preserving agents, active agents and polymers, or any other ingredient usually used in cosmetics and/or dermatology.

Needless to say, a person skilled in the art will take care to select the abovementioned optional additional compound(s) and/or the amounts thereof such that the advantageous properties intrinsically associated with the compositions in accordance with the invention are not, or are not substantially, adversely affected by the envisaged addition(s).

Among the organic solvents that may be mentioned are lower alcohols and polyols. These polyols may be chosen from glycols and glycol ethers, for instance ethylene glycol, propylene glycol, butylene glycol, dipropylene glycol or diethylene glycol.

According to one particular form of the invention, when the compositions are aqueous, the aqueous phase may also comprise a polyol that is miscible with water at room temperature (25° C.) chosen especially from polyols especially containing from 2 to 20 carbon atoms, preferably containing from 2 to 10 carbon atoms and preferentially containing from 2 to 6 carbon atoms, such as glycerol, propylene glycol, butylene glycol, pentylene glycol, hexylene glycol, dipropylene glycol or diethylene glycol; glycol ethers (especially containing from 3 to 16 carbon atoms) such as mono-, di- or tripropylene glycol ($C_1$-$C_4$)alkyl ethers, mono-, di- or triethylene glycol ($C_1$-$C_4$)alkyl ethers; and mixtures thereof.

The composition according to the invention may comprise a polyol that is miscible with water at room temperature. Such polyols may promote the moisturization of the surface of the skin on which the composition is applied.

In addition, the composition according to the invention may comprise a monoalcohol containing from 2 to 6 carbon atoms, such as ethanol or isopropanol.

Thickeners that may be mentioned include carboxyvinyl polymers, such as Carbopols (Carbomers) and the Pemulens (acrylate/$C_{10}$-$C_{30}$ alkyl acrylate copolymer); polyacrylamides, for instance the crosslinked copolymers sold under the names Sepigel 305 (CTFA name: polyacrylamide/$C_{13-14}$ isoparaffin/Laureth 7) or Simulgel 600 (CTFA name: acrylamide/sodium acryloyldimethyltaurate copolymer/isohexadecane/polysorbate 80) by the company SEPPIC; 2-acrylamido-2-methylpropanesulfonic acid polymers and copolymers, optionally crosslinked and/or neutralized, for instance poly(2-acrylamido-2-methylpropanesulfonic acid) sold by the company Hoechst under the trade name Hostacerin AMPS® (CTFA name: ammonium polyacryloyldimethyl taurate or Simulgel 800 sold by the company SEPPIC (CTFA name: sodium polyacryolyldimethyl taurate/polysorbate 80/sorbitan oleate); copolymers of 2-acrylamido-2-methylpropanesulfonic acid and of hydroxyethyl acrylate, for instance Simulgel NS and Sepinov EMT 10 sold by the company SEPPIC; cellulose derivatives such as hydroxyethyl cellulose; polysaccharides and especially gums such as xanthan gum; water-soluble or water-dispersible silicone derivatives, for instance acrylic silicones, polyether silicones and cationic silicones, and mixtures thereof.

When the compositions of the invention comprise at least one aqueous phase, they may contain acidifying agents and/or basifying agents.

Among the acidifying agents, examples that may be mentioned include mineral or organic acids, for instance hydrochloric acid, orthophosphoric acid, sulfuric acid, carboxylic acids, for instance acetic acid, tartaric acid, citric acid or lactic acid, and sulfonic acids.

Among the basifying agents, examples that may be mentioned include aqueous ammonia, alkali metal carbonates, alkanolamines, such as mono-, di- and triethanolamines and derivatives thereof, sodium hydroxide, potassium hydroxide and the compounds of formula (VI) below:

(VI)

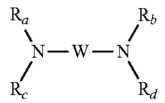

in which W is a propylene residue optionally substituted with a hydroxyl group or a $C_1$-$C_4$ alkyl radical; and $R_a$, $R_b$, $R_c$ and $R_d$, which may be identical or different, represent a hydrogen atom or a $C_1$-$C_4$ alkyl or $C_1$-$C_4$ hydroxyalkyl radical.

Preferably, the cosmetic composition comprises one or more basifying agents selected from alkanolamines, in particular triethanolamine, and sodium hydroxide.

The pH of the composition in accordance with the invention is generally between 3 and 12 approximately, preferably between 5 and 11 approximately and even more particularly from 6 to 8.5.

Among the active agents, mention may be made of:

- vitamins and derivatives or precursors thereof, alone or as mixtures;
- antioxidants;
- free-radical scavengers;
- antiglycation agents;
- calmatives;
- NO-synthase inhibitors;
- agents for stimulating the synthesis of dermal or epidermal macromolecules and/or for preventing their degradation;
- agents for stimulating fibroblast proliferation;
- agents for stimulating keratinocyte proliferation;
- muscle relaxants;
- tensioning agents;
- matting agents;
- keratolytic agents;
- desquamating agents;
- moisturizers;
- anti-inflammatory agents;
- agents that act on the energy metabolism of cells;
- insect repellents;
- substance P or CGRP antagonists;
- agents for combating hair loss and/or for the regrowth of the hair;
- anti-wrinkle agents.

A person skilled in the art will choose the said active agent or agents according to the effect desired on the skin, hair, eyelashes, eyebrows or nails.

Additional Uv-Screening Agents

The compositions according to the invention may comprise additional UV-screening agents chosen from:

- insoluble organic screening agents,
- inorganic screening agents,
- screening agents consisting of composite particles comprising an organic or inorganic matrix and an inorganic UV-screening agent,
- hydrophilic UV-A and/or UV-B organic screening agents,
- mixtures thereof.

The term "insoluble UV-screening agent" is understood to mean any UV-screening agent capable of being in the form of particles in a liquid fatty phase and in a liquid aqueous phase.

a) Insoluble Organic UV-Screening Agents

Among the organic insoluble screening agents, mention may be made of those described in patent applications U.S. Pat. Nos. 5,237,071, 5,166,355, GB 2 303 549, DE 197 26 184 and EP 893 119, especially methylenebis(hydroxyphenylbenzotriazole) derivatives such as methylenebis(benzotriazolyl)tetramethylbutylphenol sold in solid form under the trade name Mixxim BB/100 by Fairmount Chemical or in micronized form in aqueous dispersion under the trade name Tinosorb M by BASF.

Mention may also be made of the symmetrical triazine screening agents described in patent U.S. Pat. No. 6,225,467, patent application WO 2004/085412 (see compounds 6 and 9) or the document "Symmetrical Triazine Derivatives" IPCOM000031257 Journal, IP.COM INC West Henrietta, NY, US (20 Sep. 2004), especially 2,4,6-tris(di-phenyl)-triazine) and 2,4,6-tris(ter-phenyl)-triazine which is also mentioned in Beiersdorf patent applications WO 06/035 000, WO 06/034 982, WO 06/034 991, WO 06/035 007, WO 2006/034 992 and WO 2006/034 985; those compounds are preferably used in the micronized form (average size from 0.02 to 3 μm) which may be obtained for instance according to the micronization process as disclosed in the patent applications GB-A-2 303 549 et EP-A-893119 and particularly under the form of aqueous dispersion.

Mention may also be made of the compound 1,1'-(1,4-piperazinediyl) bis[1-[2-[4-(diethylamino)-2-hydroxybenzoyl]phenyl]-methanone (CAS 919803-06-8) as disclosed in the application WO2007/071584; this compound being preferably used under the micronized form (average size from 0.02 to 2 μm) which may be obtained for instance according to the micronization process as disclosed in the patent applications GB-A-2 303 549 et EP-A-893119 and particularily under the form of aqueous dispersion.

b) Inorganic UV-Screening Agents

The inorganic UV-screening agents used in accordance with the present invention are metal oxide pigments.

According to one particular form of the invention, the inorganic UV-screening agents of the invention are metal oxide pigments with a mean elemental particle size of less than or equal to 0.5 μm, more preferentially between 0.005 and 0.5 μm and even more preferentially between 0.01 and 0.1 μm, and preferentially between 0.015 and 0.05 μm.

The term "mean size" of the particles is understood to mean the parameter D[4.3] measured using a "Mastersizer 2000" particle size analyser (Malvern). The light intensity scattered by the particles as a function of the angle at which they are lit is converted to size distribution according to Mie theory. The parameter D[4.3] is measured; this is the mean diameter of the sphere having the same volume as the particle. For a spherical particle, reference will often be made to the "mean diameter".

The expression "mean elementary size" is understood to mean the size of non-aggregated particles.

They may be chosen especially from titanium oxide, zinc oxide, iron oxide, zirconium oxide and cerium oxide, or mixtures thereof, and more particularly titanium oxides.

Such coated or uncoated metal oxide pigments are described in particular in patent application EP-A-0 518 773. Commercial pigments that may be mentioned include the products sold by the companies Kemira, Tayca, Merck and Degussa.

The metal oxide pigments may be coated or uncoated.

The coated pigments are pigments that have undergone one or more surface treatments of chemical, electronic, mechanochemical and/or mechanical nature with compounds such as amino acids, beeswax, fatty acids, fatty alcohols, anionic surfactants, lecithins, sodium, potassium, zinc, iron or aluminium salts of fatty acids, metal alkoxides (of titanium or aluminium), polyethylene, silicones, proteins (collagen, elastin), alkanolamines, silicon oxides, metal oxides or sodium hexametaphosphate.

The coated pigments are more particularly titanium oxides that have been coated:

with silica, such as the product Sunveil from the company Ikeda, with silica and iron oxide, such as the product Sunveil F from the company Ikeda, with silica and alumina, such as the products Microtitanium Dioxide MT 500 SA and Microtitanium Dioxide MT 100 SA from the company Tayca and Tioveil from the company Tioxide, with alumina, such as the products Tipaque TTO-55 (B) and Tipaque TTO-55 (A) from the company Ishihara and UVT 14/4 from the company Kemira, with alumina and aluminium stearate, such as the products Microtitanium Dioxide MT 100 T, MT 100 TX, MT 100 Z and MT-01 from the company Tayca, the products Solaveil CT-10 W and Solaveil CT 100 from the company Uniqema and the product Eusolex T-AVO from the company Merck, with silica, alumina and alginic acid, such as the product MT-100 AQ from the company Tayca, with alumina and aluminium laurate, such as the product Microtitanium Dioxide MT 100 S from the company Tayca, with iron oxide and iron stearate, such as the product Microtitanium Dioxide MT 100 F from the company Tayca, with zinc oxide and zinc stearate, such as the product BR 351 from the company Tayca, with silica and alumina and treated with a silicone, such as the products Microtitanium Dioxide MT 600 SAS, Microtitanium Dioxide MT 500 SAS or Microtitanium Dioxide MT 100 SAS from the company Tayca, with silica, alumina and aluminium stearate and treated with a silicone, such as the product STT-30-DS from the company Titan Kogyo, with silica and treated with a silicone, such as the product UV-Titan X 195 from the company Kemira, with alumina and treated with a silicone, such as the products Tipaque TTO-55 (S) from the company Ishihara or UV Titan M 262 from the company Kemira, with triethanolamine, such as the product STT-65-S from the company Titan Kogyo, with stearic acid, such as the product Tipaque TTO-55 (C) from the company Ishihara, with sodium hexametaphosphate, such as the product Microtitanium Dioxide MT 150 W from the company Tayca.

$TiO_2$ treated with octyltrimethylsilane, sold under the trade name T 805 by the company Degussa Silices, $TiO_2$ treated with a polydimethylsiloxane, sold under the trade name 70250 Cardre UF $TiO_2SI_3$ by the company Cardre, anatase/rutile $TiO_2$ treated with a polydimethylhydrosiloxane, sold under the trade name Microtitanium Dioxide USP Grade Hydrophobic by the company Color Techniques.

The uncoated titanium oxide pigments are sold, for example, by the company Tayca under the trade names Microtitanium Dioxide MT 500 B or Microtitanium Dioxide MT 600 B, by the company Degussa under the name P 25, by the company Wackherr under the name Transparent titanium oxide PW, by the company Miyoshi Kasei under the name UFTR, by the company Tomen under the name ITS and by the company Tioxide under the name Tioveil AQ.

The uncoated zinc oxide pigments are for example:

those sold under the name Z-Cote by the company Sunsmart;

those sold under the name Nanox by the company Elementis;

those sold under the name Nanogard WCD 2025 by the company Nanophase Technologies.

The coated zinc oxide pigments are for example:

those sold under the name Zinc Oxide CS-5 by the company Toshibi (ZnO coated with polymethylhydrogenosiloxane);

those sold under the name Nanogard Zinc Oxide FN by the company Nanophase Technologies (as a 40% dispersion in Finsolv TN, $C_{12}$-$C_{15}$ alkyl benzoate);

those sold under the name Daitopersion Zn-30 and Daitopersion Zn-50 by the company Daito (dispersions in cyclopolymethylsiloxane/oxyethylenated polydimethylsiloxane, containing 30% or 50% of nanozinc oxides coated with silica and polymethylhydrogenosiloxane);

those sold under the name NFD Ultrafine ZnO by the company Daikin (ZnO coated with perfluoroalkyl phosphate and copolymer based on perfluoroalkylethyl as a dispersion in cyclopentasiloxane);

those sold under the name SPD-Z1 by the company Shin-Etsu (ZnO coated with silicone-grafted acrylic polymer, dispersed in cyclodimethylsiloxane);

those sold under the name Escalol Z100 by the company ISP (alumina-treated ZnO dispersed in an ethylhexyl copolymer/methicone mixture); methoxycinnamate/PVP-hexadecene those sold under the name Fuji ZnO-SMS-10 by the company Fuji Pigment (ZnO coated with silica and polymethylsilsesquioxane);

those sold under the name Nanox Gel TN by the company Elementis (ZnO dispersed at a concentration of 55% in $C_{12}$-$C_{15}$ alkyl benzoate with hydroxystearic acid polycondensate).

The uncoated cerium oxide pigments may be, for example, those sold under the name Colloidal Cerium Oxide by the company Rhône-Poulenc.

The uncoated iron oxide pigments are sold, for example, by the company Arnaud under the names Nanogard WCD 2002 (FE 45B), Nanogard Iron FE 45 BL AQ, Nanogard FE 45R AQ and Nanogard WCD 2006 (FE 45R) or by the company Mitsubishi under the name TY-220.

The coated iron oxide pigments are sold, for example, by the company Arnaud under the names Nanogard WCD 2008 (FE 45B FN), Nanogard WCD 2009 (FE 45B 556), Nanogard FE 45 BL 345 and Nanogard FE 45 BL or by the company BASF under the name Transparent Iron Oxide.

Mention may also be made of mixtures of metal oxides, in particular of titanium dioxide and of cerium dioxide, including the equal-weight mixture of titanium dioxide and cerium dioxide coated with silica, sold by the company Ikeda under the name Sunveil A, and also the mixture of titanium dioxide and zinc dioxide coated with alumina, silica and silicone, such as the product M 261 sold by the company Kemira, or coated with alumina, silica and glycerol, such as the product M 211 sold by the company Kemira.

According to the invention, coated or uncoated titanium oxide pigments are particularly preferred.

c) Screening Composite Particles

According to one particular form of the invention, the additional screening agents may consist of composite particles comprising an organic and/or inorganic matrix and an inorganic UV-screening agent.

These composite particles preferably have a mean size of between 0.1 and 30 μm and comprise a matrix and an inorganic UV-screening agent, the content of inorganic screening agent in a particle ranging from 1% to 70% by weight.

These composite particles can be chosen from spherical composite particles, lamellar composite particles or their mixtures.

The composite particles used according to the present invention comprise a matrix and an inorganic UV-screening agent. The matrix comprises one or more organic and/or inorganic materials.

The inorganic UV-screening agent is generally chosen from metal oxides, preferably titanium, zinc or iron oxides, or mixtures thereof and more particularly from titanium dioxide, zinc oxide and mixtures thereof. Particularly preferably, the inorganic UV-screening agent is $TiO_2$.

These metal oxides may be in the form of particles, having a mean elementary size generally of less than 200 nm. Advantageously, the metal oxide particles used have a mean elementary size of less than or equal to 0.1 μm.

These metal oxides may also be in the form of layers, preferably multilayers with a mean thickness generally of less than 0.2 μm.

According to a first variant, the composite particles contain a matrix comprising an organic and/or inorganic material, in which matrix particles of inorganic UV-screening agent are included. According to this embodiment, the matrix has inclusions and particles of inorganic UV-screening agent are placed in the inclusions of the matrix.

According to a second variant, the composite particles contain a matrix made of an organic and/or inorganic material, which matrix is covered with at least one layer of inorganic UV-screening agent which may be connected to the matrix with the aid of a binder.

According to a third variant, the composite particles contain an inorganic UV-screening agent covered with at least one layer of an organic and/or inorganic material.

The matrix may also be formed from one or more organic or inorganic materials. It may then be a continuous phase of materials such as an alloy, i.e. a continuous phase in which the materials can no longer be dissociated, or a discontinuous phase of materials, for example constituted of an organic or inorganic material covered with a layer of another different organic or inorganic material.

The weight content of metal oxide in the particles of the invention is between 1% and 70%, preferably between 2% and 65%, and better still between 3% and 60%.

According to one variant, in particular when the composite particles comprise a matrix covered with a layer of UV-screening agent, the composite particles may furthermore be covered with an additional coating, in particular chosen from biodegradable or biocompatible materials, lipid materials, for instance surfactants or emulsifiers, polymers, and oxides.

The screening composite particles may be chosen from those of spherical shape, those of non-spherical shape, or mixtures thereof.

The term "spherical" is understood to mean that the particle has a sphericity index, i.e. the ratio between its largest diameter and its smallest diameter, of less than 1.2.

The term "non-spherical" is understood to mean particles having three dimensions (length, width and thickness or height) for which the ratio of the largest dimension to the smallest dimension is greater than 1.2. The dimensions of the particles of the invention are evaluated by scanning electron microscopy and image analysis. They include particles of parallelepipedal shape (rectangular or square surface area), discoid shape (circular surface area) or ellipsoid shape (oval surface area), characterized by three dimensions: a length, a width and a height. When the shape is circular, the length and the width are identical and correspond to the diameter of a disc, whereas the height corresponds to the thickness of the disc. When the surface is oval, the length and the width correspond, respectively, to the large axis and the small axis of an ellipse and the height corresponds to the thickness of the elliptic disc formed by the platelet. When it is a parallelepiped, the length and the width may be of identical or different dimensions: when they are of the same dimension, the shape of the surface of the parallelepiped is a square; in the contrary case, the shape is rectangular. As regards the height, it corresponds to the thickness of the parallelepiped.

Preferably, the content of composite particles of the composition according to the invention ranges from 1% to 70%, preferably from 1.5% to 45%, preferably from 2% to 20% by weight relative to the total weight of the cosmetic composition.

Spherical Screening Composite Particles

The inorganic materials that may be used in the matrix of the spherical composite particles according to the present invention may be chosen from the group formed by glass, silica and aluminium oxide, and mixtures thereof.

The organic materials that may be used to form the matrix are chosen from the group formed by poly(meth)acrylates, polyamides, silicones, polyurethanes, polyethylenes, polypropylenes, polystyrenes, polycaprolactams, polysaccharides, polypeptides, polyvinyl derivatives, waxes, polyesters, polyethers, and mixtures thereof.

Preferably, the matrix of the spherical composite particle contains a material or mixture of materials chosen from:

- $SiO_2$,
- polymethyl methacrylate,
- copolymers of styrene and of a $C_1/C_5$ alkyl (meth)acrylate derivative,
- polyamides, such as nylon.

The composite particles in spherical form are characterized by a mean diameter between 0.1 and 30 μm, preferably between 0.2 and 20 μm and more preferably between 0.3 and 10 μm, advantageously between 0.5 and 10 μm.

According to a first variant, the spherical composite particles contain a matrix comprising an organic and/or inorganic material, in which matrix particles of inorganic UV-screening agent are included.

According to this first variant, the particles of inorganic UV-screening agent are characterized by a mean elementary size generally of less than 200 nm. Advantageously, the metal oxide particles used have a mean elementary size of less than or equal to 0.1 μm.

As composite particles corresponding to this variant, mention may be made of the products Sunsil TIN 50 and Sunsil TIN 40 sold by the company Sunjin Chemical. These spherical composite particles having a mean size between 2 and 7 μm are formed of $TiO_2$ encapsulated in a silica matrix.

Mention may also be made of the following particles:

- spherical composite particles having a mean size between 4 and 8 μm, containing $TiO_2$ and $SiO_2$ and having the trade name Eospoly TR sold by the company Creations Couleurs,
- composite particles comprising $TiO_2$ and a styrene/alkyl acrylate copolymer matrix, sold under the name Eospoly UV TR22 HB 50 by Creations Couleurs,
- composite particles comprising $TiO_2$ and ZnO and a PMMA matrix and having the trade name Sun PMMA-T50, sold by Sunjin Chemical.

According to a second alternative form, the spherical composite particles contain a matrix made of an organic and/or inorganic material, which matrix is covered with at least one layer of inorganic UV-screening agent connected to the matrix with the aid of a binder.

According to this second variant, the mean thickness of the layer of inorganic UV-screening agent is generally between 0.001 and 0.2 μm and preferably between 0.01 and 0.1 μm.

The spherical composite particles used according to the invention have a size of between 0.1 and 30 μm, preferably between 0.3 and 20 μm and even more preferentially between 0.5 and 10 μm.

Among the composite particles that may be used according to the invention, mention may also be made of spherical composite particles containing $TiO_2$ and $SiO_2$, having the trade name STM ACS-0050510, supplied by the company JGC Catalysts and Chemical.

According to a third variant, the spherical composite particles contain an inorganic UV-screening agent covered with at least one layer of an organic and/or inorganic material. According to this third variant, the particles of inorganic UV-screening agent are characterized by a mean elementary size generally of between 0.001 and 0.2 μm. Advantageously, the metal oxide particles used have a mean elementary size between 0.01 and 0.1 μm.

The spherical composite particles used according to the invention have a size of between 0.1 and 30 μm, preferably between 0.3 and 20 μm and even more preferentially between 0.5 and 10 μm.

Non-Spherical Screening Composite Particles

The organic materials that may be used to form the matrix of the non-spherical screening particles are chosen from the group formed by polyamides, silicones, polysaccharides, polyvinyl derivatives, waxes and polyesters, and mixtures thereof.

Among the organic materials that may be used, mention is preferably made of:

- triethoxycaprylylsilane,
- ethylene/vinyl acetate copolymers.

The inorganic materials that may be used in the matrix of the non-spherical composite particles are chosen from the group formed by mica, synthetic mica, talc, silica, aluminium oxide, boron nitride, kaolin, hydrotalcite, mineral clays and synthetic clays, and mixtures thereof. Preferably, these inorganic materials are chosen from:

- silica,
- talc;
- mica;
- alumina.

The non-spherical composite particles of the invention are characterized by three dimensions, of which:

- the smallest is greater than 0.1 μm, preferably greater than 0.3 μm and better still greater than 0.5 μm;
- the largest is less than 30 micrometres, preferably 20 micrometres and better still 10 micrometres.

The ratio of the largest to the smallest dimension is greater than 1.2.

The dimensions of the particles of the invention are evaluated by scanning electron microscopy and image analysis.

The non-spherical screening composite particles that may be used according to the invention will preferably be platelet-shaped.

The term "platelet-shaped" means parallelepipedal-shaped.

They may be smooth, rough or porous.

The platelet-shaped composite particles preferably have a mean thickness of between 0.1 and 10 μm, the mean length is generally between 0.5 and 30 μm and the mean width is between 0.5 and 30 μm.

The thickness is the smallest of the dimensions, the width is the medium dimension, and the length is the longest of the dimensions.

According to a first variant, the composite particles contain a matrix comprising an organic and/or inorganic material, in which matrix particles of inorganic UV-screening agent are included.

According to this first variant, the particles of inorganic UV-screening agent are characterized by a mean elementary size generally of less than 0.2 μm. Advantageously, the metal oxide particles used have a mean elementary size of less than or equal to 0.1 μm.

According to a second variant, the composite particles contain a matrix made of an organic and/or inorganic material, which matrix is covered with at least one layer of inorganic UV-screening agent connected to the matrix with the aid of a binder.

According to this second variant, the mean thickness of the layer of inorganic UV-screening agent is generally about ten nanometres. The mean thickness of the layer of inorganic UV-screening agent is advantageously between 0.001 and 0.2 μm, preferably between 0.01 and 0.2 μm.

According to a third variant, the non-spherical composite particles contain an inorganic UV-screening agent covered with at least one layer of an organic and/or inorganic material. According to this third variant, the particles of inorganic UV-screening agent are characterized by a mean elementary size generally of between 0.001 and 0.2 μm. Advantageously, the metal oxide particles used have a mean elementary size between 0.01 and 0.1 μm.

The non-spherical composite particles used according to the invention have a size of between 0.1 and 30 μm and preferably between 0.5 and 10 μm.

Preferably, the inorganic UV-screening agent used in the composite particle is chosen from metal oxides, in particular from titanium, zinc or iron oxides and more particularly titanium dioxide ($TiO_2$).

Preferably, the matrix of the composite particle contains a material or a mixture of materials chosen from:

$SiO_2$,
alumina,
mica,
alumina/triethoxycaprylylsilane mixture,
talc;
Nylon.

More preferably, the matrix of the composite particle is formed from a material or mixture of materials chosen from:

alumina,
alumina/triethoxycaprylylsilane mixture;
talc,
silica,
mica.

Among the composite particles that may be used according to the invention, mention may also be made of the following particles:

- composite particles containing $TiO_2$ and an alumina matrix, of trade name Matlake OPA sold by the company Sensient LCW,
- composite particles comprising $TiO_2$ and an alumina/triethoxycaprylylsilane matrix, with the trade name Matlake OPA AS, sold by the company Sensient LCW,
- composite particles comprising ultrafine $TiO_2$ particles deposited on the surface of talc platelets, with the trade name TTC 30, sold by the company Miyoshi Kasei,
- composite particles containing ultrafine $TiO_2$ particles deposited on the surface of talc platelets, of trade name Silseem Mistypearl Yellow sold by the company Nihon Koken Kogyo (NKK).

d) Hydrophilic UV-A and/or UV-B Organic Screening Agents

When the compositions of the invention comprise at least one aqueous phase, they may also contain one or more hydrophilic UV-A and/or UV-B organic screening agents.

The term "hydrophilic organic UV-screening agent" means an organic molecule that is capable of screening out UV radiation between 290 and 400 nm, and which can be dissolved in molecular form or dispersed in an aqueous phase in order to obtain a macroscopically homogeneous phase.

Among the hydrophilic UV-A UV-screening agents that are capable of absorbing UV from 320 to 400 nm, mention may be made of:

- Terephthalylidenedicamphorsulfonic acid manufactured under the name Mexoryl SX by Chimex,
- Bis-benzazolyl derivatives as described in patents EP 669 323, and U.S. Pat. No. 2,463,264 and more particularly the compound disodium phenyldibenzimidazoletetrasulfonate sold under the trade name Neo Heliopan AP by Haarmann & Reimer.

Among the hydrophilic UVB UV-screening agents that are capable of absorbing UV from 280 to 320 nm, mention may be made of:

- p-aminobenzoic acid (PABA) derivatives such as
  - PABA,
  - Glyceryl PABA, and
  - PEG-25 PABA sold under the name Uvinul P25 by BASF,
- Phenylbenzimidazolesulfonic acid sold in particular under the trade name Eusolex 232 by Merck,
- ferulic acid,
- p-methoxycinnamic acid,
- DEA methoxycinnamate,
- benzylidenecamphorsulfonic acid manufactured under the name Mexoryl SL by Chimex,
- camphorbenzalkonium methosulfate manufactured under the name Mexoryl SO by Chimex.

Among the hydrophilic UVA and UVB UV-screening agents, mention may be made of:

- Benzophenone-4 sold under the trade name Uvinul MS40 by BASF,
- Benzophenone-5, and
- Benzophenone-9.

The additional UV-screening agents are generally present in the compositions according to the invention in proportions ranging from 0.01% to 20% by weight relative to the total weight of the composition, and preferably ranging from 0.1% to 10% by weight relative to the total weight of the composition.

Assembly

According to another aspect, the invention also relates to a cosmetic assembly comprising:

i) a container delimiting one or more compartment(s), the said container being closed by a closing member and optionally not being leaktight; and ii) a makeup and/or care composition in accordance with the invention placed inside the said compartment(s).

The container may be, for example, in the form of a jar or a box.

The closing member may be in the form of a lid comprising a cap mounted so as to be able to move by translation or by pivoting relative to the container housing the said makeup and/or care composition(s).

The examples that follow serve to illustrate the invention without, however, being limiting in nature. In these examples, the amounts of the composition ingredients are given as weight percentages relative to the total weight of the composition.

Examples 1 to 3: Antisun Oils

| Phase | INCI name | Example 1 (invention) | Example 2 (outside the invention) |
|---|---|---|---|
| A1 | $C_{12-15}$ Alkyl benzoate | 10 | 10 |
| | Diisopropyl sebacate | 5 | 5 |
| | Octyldodecanol | 26 | 26 |
| | Caprylic capric triglyceride | 26 | 26 |
| | Butylmethoxydibenzoylmethane | 1.5 | 1.5 |
| | Bis(ethylhexyloxyphenol)methoxy-phenyltriazine | 1.5 | 1.5 |
| | Drometrizole trisiloxane | 1 | 1 |
| | Ethylhexyl triazone | 1.7 | 1.7 |
| A2 | Silica silylate (Dow Corning VM-2270 Aerogel Fine Particles) | 3.5 | — |
| | Silica dimethyl silylate (Aerosil R 972) | — | 3.5 |
| A3 | Isododecane | 6 | 6 |
| | Isohexadecane | 5.3 | 5.3 |
| | Denatured alcohol | 12.5 | 12.5 |

| Phase | INCI name | Example 3 (outside the invention) |
|---|---|---|
| A1 | $C_{12-15}$ Alkyl benzoate | 10 |
| | Diisopropyl sebacate | 5 |
| | Octyldodecanol | 26 |
| | Caprylic capric triglyceride | 26 |
| | Butylmethoxydibenzoylmethane | 1.5 |
| | Bis(ethylhexyloxyphenol)methoxy-phenyltriazine | 1.5 |
| | Drometrizole trisiloxane | 1 |
| | Ethylhexyl triazone | 1.7 |
| A2 | Polystearyl acrylate (Intelimer IPA 13-1 from Air Products) | 3.5 |
| A3 | Isododecane | 6 |
| | Isohexadecane | 5.3 |
| | Denatured alcohol | 12.5 |

Oil Preparation Method:

The oil phase A1 is prepared by mixing together the starting materials with mechanical mixing at 80° C. Once the solution is macroscopically homogeneous and translucent, phase A2 is added thereto with stirring. The solution obtained is cooled to room temperature, followed by introducing phase A3. The final solution is macroscopically homogeneous, and more or less transparent depending on the content of Aerogel hydrophobic silica.

Examples 4 to 7: Oil/Water Emulsions

| Phase | INCI name | Example 4 | Example 5 (outside the invention) |
|---|---|---|---|
| A1 | Stearic acid | 1.5 | 1.5 |
| | Glyceryl stearate and PEG-100 stearate | 1.5 | 1.5 |
| | Methylparaben | 0.2 | 0.2 |
| | $C_{12-15}$ Alkyl benzoate | 2.9 | 2.9 |
| | Diisopropyl sebacate | 1.45 | 1.45 |
| | Octyldodecanol | 7.54 | 7.54 |
| | Caprylic capric triglyceride | 7.54 | 7.54 |
| | Butylmethoxydibenzoylmethane | 1.64 | 1.64 |
| | Bis(ethylhexyloxyphenol)methoxy-phenyltriazine | 1.64 | 1.64 |
| | Drometrizole trisiloxane | 1.09 | 1.09 |
| | Ethylhexyl triazone | 1.85 | 1.85 |
| A2 | Silica silylate (Dow Corning VM-2270 Aerogel Fine Particles) | 3.82 | — |
| B | Water | qs 100 | qs 100 |
| | Disodium EDTA | 0.1 | 0.1 |
| | Glycerol | 6 | 6 |
| | Propylene glycol | 6 | 6 |
| | Potassium cetyl phosphate | 1 | 1 |
| | Caprylyl glycol | 0.4 | 0.4 |
| | Phenoxyethanol | 0.7 | 0.7 |
| | Triethanolamine | 1.05 | 1.05 |
| | Terephthalylidenedicamphor-sulfonic acid | 1 | 1 |
| | Acrylates/$C_{10-30}$ Alkyl Acrylate Crosspolymer | 0.4 | 0.4 |
| C | Denatured alcohol | 6.9 | 6.9 |

| Phase | INCI name | Example 6 (outside the invention) | Example 7 (outside the invention) |
|---|---|---|---|
| A1 | Stearic acid | 1.5 | 1.5 |
| | Glyceryl stearate and PEG-100 stearate | 1.5 | 1.5 |
| | Methylparaben | 0.2 | 0.2 |
| | $C_{12-15}$ Alkyl benzoate | 2.9 | 2.9 |
| | Diisopropyl sebacate | 1.45 | 1.45 |
| | Octyldodecanol | 7.54 | 7.54 |
| | Caprylic capric triglyceride | 7.54 | 7.54 |
| | Butylmethoxydibenzoylmethane | 1.64 | 1.64 |
| | Bis(ethylhexyloxyphenol)methoxy-phenyltriazine | 1.64 | 1.64 |
| | Drometrizole trisiloxane | 1.09 | 1.09 |
| | Ethylhexyl triazone | 1.85 | 1.85 |
| A2 | Silica dimethyl silylate (Aerosil R 972) | 3.82 | |
| | Ethylenediamine/stearyl dimer dilinoleate copolymer | — | 3.82 |
| B | Water | qs 100 | qs 100 |
| | Disodium EDTA | 0.1 | 0.1 |
| | Glycerol | 6 | 6 |
| | Propylene glycol | 6 | 6 |
| | Potassium cetyl phosphate | 1 | 1 |
| | Caprylyl glycol | 0.4 | 0.4 |
| | Phenoxyethanol | 0.7 | 0.7 |
| | Triethanolamine | 1.05 | 1.05 |
| | Terephthalylidenedicamphor-sulfonic acid | 1 | 1 |
| | Acrylates/$C_{10-30}$ Alkyl Acrylate Crosspolymer | 0.4 | 0.4 |
| C | Denatured alcohol | 6.9 | 6.9 |

Emulsion Preparation Method:

The oil phase A1 is prepared by mixing together the starting materials with mechanical stirring at 80° C. A2 is added to the first phase as soon as it becomes homogeneous and transparent. In parallel, the aqueous phase B is also stirred at 80° C. Once the oil solution A and the aqueous solution B are macroscopically homogeneous, the emulsion is prepared by introducing phase A into phase B with stirring using a rotor-stator homogenizer at a stirring speed of 4500 rpm for 20 minutes. The emulsion is cooled to room temperature before adding phase C. The final emulsion is characterized by drops between 1 μm and 20 μm in size.

in vitro protocol for evaluating the screening efficacy

The sun protection factor (SPF) is determined according to the "in vitro" method described by B. L. Diffey in J. Soc. Cosmet. Chem. 40, 127-133 (1989). The measurements were made using a UV-1000S spectrophotometer from the company Labsphere. The "static in vitro protection factor (SPF)" is extracted. Each composition is applied to a rough plate of PMMA, in the form of a homogeneous and even deposit at a rate of 1 mg/cm$^2$.

The in vitro PPD index measurements are taken under the same conditions using a UV-1000S spectrophotometer from the company Labsphere. The "UV-A ppd index (persistent pigment darkening action spectrum)" value is extracted. Each composition is applied to a rough plate of PMMA, in the form of a homogeneous and even deposit at a rate of 1 mg/cm$^2$.

Results

| | Examples of antisun oils | | |
|---|---|---|---|
| | Ex. 1 (invention) | Ex. 2 (outside the invention) | Ex. 3 (outside the invention) |
| in vitro SPF | 27.1 ± 2.0 | 13.6 ± 0.9 | 14.6 ± 3.2 |
| in vitro PPD | 9.5 ± 0.5 | 6.6 ± 0.4 | 7.1 ± 1.0 |

| | Examples of O/W antisun emulsions | | | |
|---|---|---|---|---|
| | Ex. 4 (invention) | Ex. 5 (outside the invention) | Ex. 6 (outside the invention) | Ex. 7 (outside the invention) |
| In vitro SPF | 29.4 ± 3.9 | 16.0 ± 3.9 | 19.5 ± 1.0 | 18.9 ± 1.4 |
| in vitro PPD | 14.1 ± 1.5 | 8.6 ± 1.1 | 9.7 ± 0.5 | 10.2 ± 0.7 |

These results show that compositions 1 and 4 of the invention make it possible to obtain a higher level of screening efficacy than compositions 2 and 6 comprising Aerosil particles, than compositions 3 and 7 comprising a fatty-phase-gelling polymer.

For composition 5 not containing any hydrophobic silica aerogel particles, the performance qualities in terms of screening efficacy are inferior to those of the compositions of the invention.

The invention claimed is:

1. A non-pulverulent antisun composition consisting essentially of, in a cosmetically acceptable medium:

a) at least one oil phase containing:

(i) at least one non-volatile polar hydrocarbon-based oil in an amount of 10% to 90% by weight relative to the total weight of the composition, wherein the non-volatile hydrocarbon-based polar oil is chosen from caprylic/capric acid triglycerides, $C_{12}$-$C_{15}$ alkyl benzoates, diisopropyl sebacate, isopropyl lauroyl sarcosinate, dicaprylyl carbonate, the 2-phenylethyl ester of benzoic acid, butyloctyl salicylate, octyldodecanol, 2-octyldodecyl neopentanoate, dicaprylyl ether, isocetyl stearate, isodecyl neopentanoate, isononyl isononate, isopropyl myristate, isopropyl palmitate, isostearyl behenate, myristyl myristate, octyl palmitate and tridecyl trimellitate, and mixtures thereof;

b) 5% to 25% by weight relative to the total weight of the composition of at least one organic lipophilic UV-screening agent, wherein the at least one lipophilic organic UV-screening agent is chosen from: Butyl Methoxy Dibenzoylmethane, Octocrylene, Ethylhexyl Salicylate, n-Hexyl 2-(4-diethylamino-2-hydroxybenzoyl)benzoate, Bis-Ethylhexyloxyphenol Methoxyphenyl Triazine, Ethylhexyl Triazone, Diethylhexyl Butamido Triazone, Drometrizole Trisiloxane, Ethylhexyl methoxycinnamate, and mixtures thereof; and c) 0.5% to 10% by weight of at least hydrophobic silica aerogel particles;

the composition comprising less than 5% by weight of non-volatile non-cyclic silicone oil relative to the total weight of the composition; and wherein the composition due to the inclusion of the hydrophobic silica aerogel particles exhibits superior sun screening efficacy as compared to composition not containing the hydrophobic silica aerogel particles.

2. The non-pulverulent antisun composition according to claim 1, wherein the hydrophobic aerogel particles have a specific surface area per unit of mass (SM) ranging from 200 to 1500 m$^2$/g expressed as the volume mean diameter (D [0.5] ), ranging from 1 to 30 μm and/or an oil-absorbing capacity, measured at the wet point, ranging from 5 to 18 ml/g of particles.

3. The non-pulverulent antisun composition according to claim 1, wherein the hydrophobic silica aerogel particles have a size, expressed as the volume mean diameter, ranging from 5 to 25 μm.

4. The non-pulverulent antisun composition according to claim 1, wherein the hydrophobic silica aerogel particles are surface modified with trimethylsilyl groups.

5. The non-pulverulent antisun composition according to claim 1, wherein the hydrophobic silica aerogel particles have a tapped density p ranging from 0.04 g/cm$^3$ to 0.10 g/cm$^3$.

6. The non-pulverulent antisun composition according to claim 1, wherein the hydrophobic silica aerogel particles have a specific surface area per unit of volume SV ranging from 5 to 60 m$^2$/cm$^3$.

7. The non-pulverulent antisun composition according to claim 1, wherein the hydrophobic silica aerogel particles have an oil-absorbing capacity, measured at the wet point, ranging from 5 to 18 ml/g.

8. The non-pulverulent antisun composition according to claim 1, wherein the lipophilic organic UV-screening agent (s) are chosen from:

Butyl Methoxy Dibenzoylmethane,
Octocrylene,
Ethylhexyl Salicylate,
n-Hexyl 2-(4-diethylamino-2-hydroxybenzoyl)benzoate,
Bis-Ethylhexyloxyphenol Methoxyphenyl Triazine,
Ethylhexyl Triazone,
Diethylhexyl Butamido Triazone,
Drometrizole Trisiloxane, and mixtures thereof.

9. The non-pulverulent antisun composition according to claim 1, which comprises at least one additional UV-screening agent chosen from:

insoluble organic screening agents,
inorganic screening agents,
screening agents consisting of composite particles comprising an organic or inorganic matrix and an inorganic UV-screening agent,
hydrophilic UV-A and/or UV-B organic screening agents,
mixtures thereof.

10. The non-pulverulent antisun composition according to claim 1, which is in the form of an anhydrous composition.

11. The non-pulverulent antisun composition according to claim 1, which also comprises at least one aqueous phase.

12. The non-pulverulent antisun composition according to claim 1, wherein the non-volatile hydrocarbon-based polar oil is chosen from caprylic/capric acid triglycerides, $C_{12}$-$C_{15}$ alkyl benzoates, diisopropyl sebacate, isopropyl lauroyl sarcosinate, dicaprylyl carbonate, the 2-phenylethyl ester of benzoic acid, butyloctyl salicylate, 2-octyldodecyl neopentanoate, dicaprylyl ether, isocetyl stearate, isodecyl neopentanoate, isononyl isononate, isopropyl myristate, isopropyl palmitate, isostearyl behenate, myristyl myristate, octyl palmitate and tridecyl trimellitate, and mixtures thereof.

13. The non-pulverulent antisun composition according to claim 12, wherein the non-volatile hydrocarbon-based polar oil is chosen from caprylic/capric acid triglycerides, C12-C15 alkyl benzoates, diisopropyl sebacate and 2-octyldodecanol neopentanoate, and mixtures thereof.

14. The non-pulverulent antisun composition according to claim 2 wherein the hydrophobic silica aerogel particles have a size, expressed as the volume mean diameter, ranging from 5 to 25 μm.

15. The non-pulverulent antisun composition according to claim 2, wherein the hydrophobic silica aerogel particles surface-modified with trimethylsilyl groups.

16. The non-pulverulent antisun composition according to claim 3, wherein the hydrophobic silica aerogel particles are surface modified with trimethylsilyl groups.

17. The non-pulverulent antisun composition according to claim 2, wherein the hydrophobic silica aerogel particles have a tamped density ρ ranging from 0.04 $g/cm^3$ to 0.10 $g/cm^3$.

18. The non-pulverulent antisun composition according to claim 3, wherein the hydrophobic silica aerogel particles have a tapped density p ranging from 0.04 $g/cm^3$ to 0.10 $g/cm^3$.

19. The non-pulverulent antisun composition according to claim 1, which further includes a monoalcohol containing from 2 to 6 carbon atoms.

20. The non-pulverulent antisun composition according to claim 19, wherein the monoalcohol is selected from the group of ethanol, isopropanol and mixtures thereof.

21. The non-pulverulent antisun composition according to claim 19, wherein the monoalcohol comprises denatured alcohol.

22. The non-pulverulent antisun composition according to claim 1, which further comprises a volatile hydrocarbon-based oil selected from the group of branched $C_8$-$C_{16}$ alkanes.

23. The non-pulverulent antisun composition according to claim 22, wherein volatile hydrocarbon-based oil is selected from the group of isododecane, isodecane, isohexadecane and mixtures thereof.

24. A cosmetic process for caring for and/or making up human keratin materials comprising at least the application, to the surface of the keratin material, of at least one non-pulverulent antisun composition as defined according to claim 1.

* * * * *